(12) United States Patent
Schaefer et al.

(10) Patent No.: US 9,220,884 B2
(45) Date of Patent: Dec. 29, 2015

(54) MULTI-CONNECTOR AND MEDICAL DEVICE FOR EXTRACORPOREAL BLOOD TREATMENT

(71) Applicant: B. Braun Avitum AG, Melsungen (DE)

(72) Inventors: Oliver Schaefer, Neuenstein (DE); Dirk Moeller, Altmorschen (DE); Bruno Stenzel, Hatten (DE)

(73) Assignee: B. BRAUN AVITUM AG, Melsungen (DE)

( * ) Notice: Subject to any disclaimer, the term of this patent is extended or adjusted under 35 U.S.C. 154(b) by 317 days.

(21) Appl. No.: 13/934,745

(22) Filed: Jul. 3, 2013

(65) Prior Publication Data
US 2014/0012176 A1    Jan. 9, 2014

(30) Foreign Application Priority Data

Jul. 3, 2012 (DE) .......................... 10 2012 105 917

(51) Int. Cl.
*A61M 39/10* (2006.01)
*F04B 43/12* (2006.01)
*A61M 1/36* (2006.01)

(52) U.S. Cl.
CPC ........... *A61M 39/105* (2013.01); *A61M 1/3621* (2013.01); *F04B 43/1253* (2013.01)

(58) Field of Classification Search
CPC ........... A61M 39/105; A61M 1/3621; A61M 1/3627; A61M 1/34; A61M 1/16; A61M 1/14; A61M 1/3629; A61M 2001/14; A61M 2001/32; A61M 2202/0413
USPC ................................ 604/4.01–6.16; 138/106; 417/474–477.14
See application file for complete search history.

(56) References Cited

U.S. PATENT DOCUMENTS

| 4,599,055 A | 7/1986 | Dykstra |
| 5,588,815 A * | 12/1996 | Zaleski, II .................. 417/477.2 |
| 8,047,819 B2 | 11/2011 | Lawrence et al. |

FOREIGN PATENT DOCUMENTS

DE    696 15 633    6/2002

OTHER PUBLICATIONS

German Search Report for DE 10 2012 105 917.9 dated Jan. 17, 2013.

* cited by examiner

*Primary Examiner* — Philip R Wiest
(74) *Attorney, Agent, or Firm* — RatnerPrestia (57) ABSTRACT

Multi-connectors are disclosed for arranging a tubing segment and feeding/discharging lines of an extracorporeal blood circulation on a tube roller pump, the multi-connectors including a base and connectors for connecting the tubing segment to the feeding/discharging lines. A first connector includes a convex contour. The multi-connectors may be arranged on a medical device pump housing having a bearing surface and a rotor within the bearing surface, wherein a tube can be introduced between the bearing surface and the rotor and blood can be fed/discharged via feeding/discharging lines. A concave receiving portion is provided for the first connector, forming a pivot bearing to pivot the multi-connector. Pump housing means for locking adapted to interact with multi-connector means for locking are provided so the multi-connector can be detachably fastened.

15 Claims, 7 Drawing Sheets

MULTI-CONNECTOR AND MEDICAL DEVICE FOR EXTRACORPOREAL BLOOD TREATMENT

CROSS REFERENCE TO RELATED APPLICATIONS

This application claims priority to German Patent Application No. DE 10 2012 105 917.9 filed Jul. 3, 2012, the contents of such application being incorporated by reference herein.

FIELD OF THE INVENTION

The invention relates to a multi-connector for arranging a tubing segment and feeding and discharging lines of an extracorporeal blood circulation on a tube roller pump.

The invention further relates to a medical device for extracorporeal blood treatment on which such multi-connector can be arranged.

BACKGROUND INFORMATION

In medical devices for extracorporeal blood treatment (dialysis) frequently tube roller pumps are employed for returning the blood withdrawn from the patient to a dialyser and back to the patient. Such tube roller pumps are peristaltic pumps, wherein a loop-shaped tubing segment is adjacent to an appropriately bent bearing surface of the pump housing. A rotor of the pump located inside the bearing surface then moves with its outer edges along the tubing segment, wherein the tube is locally indented and thus the elastic material properties of the tubing segment enable blood to be fed through the tubing segment. For this, the blood is fed to the tubing segment via a first port and is discharged via another port at the other end of the tubing segment. In this way, together with the feeding and discharging lines and several air traps, for instance, the tubing segment forms a transfer system, as it is called, by which the blood of the patient is fed to a dialyser and back to the patient.

Those transfer systems are preferably exchanged after each treatment and are not re-used for other patients. A used tubing segment thus need not be removed from the pump before a new transfer system is introduced to the device. In order to facilitate handling during removing and mounting the transfer system it is known to provide a connector adapted to be connected to a feeding and discharging line at each of the two ends of the tubing segment. However, such connectors are merely connecting pieces and fulfill no further functions. It is a drawback of such manual systems that confusions may occur upon insertion into the pump. This problem can be solved, for example, by color encoding and/or geometrical encoding.

Furthermore, multi-connectors are known which unify both ports for feeding and discharging lines in one component part which is then adapted to be introduced into a receiving portion of the pump housing. Due to their geometrical shape and their material properties those components frequently permit simple and unambiguous insertion of the pump segment into the pump. A geometrical encoding excludes any incorrect mounting position. However, those systems frequently lack an operating surface for inserting the system into the pump which impedes manipulation.

Moreover automatic systems intended to take over and thus facilitate threading and unthreading are known. Frequently for unthreading an actuator has to be actuated which moves the system from its therapy position into an unthreading position via a linear drive, for example. For this purpose, it may be required in such systems to operate a switch/button on the medical device or to touch a software button on a user interface.

DESCRIPTION OF THE RELATED ART

For receiving a tube inside a roller pump without connectors, U.S. Pat. No. 8,047,819 B2, for example, describes holding devices that are detachably mounted on the pump housing. Thus for different sizes and types of tubes different holding devices can be mounted on the pump. A holding device has a clamping device including at least one pivoting clamp jaw which has a semicircular recess so that a tube can be held in said semicircular recess and in an opposing equally semicircular recess of another clamp jaw. The clamp jaws may also include a plurality of said recesses so that plural tubes can be simultaneously accommodated.

SUMMARY OF THE INVENTION

It is an object of the invention to provide a connector for attaching a tubing segment and feeding and discharging lines of an extracorporeal blood circulation to a tube roller pump, which connector assists simple and safe handling of the transfer system formed at least by the tubing segment, the connector and the feeding and discharging lines.

It is another object of the invention to provide a medical device for extracorporeal blood treatment on which the transfer system formed of at least the tubing segment, the feeding and discharging lines and the connector according to aspects of the invention can be mounted.

The multi-connector according to aspects of the invention is suited for mounting a tubing segment and feeding and discharging lines of an extracorporeal blood circulation on a tube roller pump, the multi-connector having at least a base member and two connector elements for connecting the respective ends of the tubing segment to the feeding line and the discharging line. In accordance with aspects of the invention, the two connector elements are arranged on two opposing sides of the base member, the outer contour of a first connector element having at least a slide bearing portion, especially a portion including an outwardly and evenly curved outer contour, which may be a hollow cylinder portion, which when cooperating with a corresponding slide bearing portion at the pump housing of the tube roller pump, especially with an inwardly and evenly curved recess in the pump housing of the tube roller pump permits a defined pivoting motion of the multi-connector about a pivoting axis, and aside the first connector element or spaced apart from the first connector element means for locking the multi-connector with a pump housing of the tube roller pump are provided.

This structure of the multi-connector enables the first connector element to be introduced into a receiving portion at the pump housing of a tube roller pump, wherein a pivot bearing can be formed by the cylindrical area of the connector element so that the multi-connector is pivotable about the cylinder axis of the first connector element. This can be advantageously used when inserting and removing the multi-connector, the means for locking the multi-connector being provided at the pump housing aside the first connector element. Possible locking means in the area of the pivoting point are thus not considered to be means for locking the multi-connector according to claim 1 but can be additionally provided. The basic locking means serve for locking the multi-connector with the pump housing in a therapy position.

In a first embodiment of the invention the multi-connector and thus its two connectors can be fixedly connected to the tubing segment and the feeding and discharging lines of the extracorporeal blood circulation. On one side of the multi-connector the two ends of the tubing segment inserted in the tube roller pump for the pumping function are connected to the connector elements whereby a tubular loop is formed. On the other side of the multi-connector a respective feeding and discharging line is connected to each of the connector elements. These connections of the tubes to the multi-connector can be made by bonding.

In a second embodiment of the invention each of the connector elements of the multi-connector has at least one receiving portion for detachably connecting the tubing segment and the feeding and discharging lines to the multi-connector. Then the multi-connector forms a re-usable adapter connectable to a standard transfer system, for example, whereby the advantageous configuration of the multi-connector is adapted to be used for a standard transfer system as well. For instance, a tubing segment is connected to the feeding and discharging lines via individual standard connector elements, and the tubing segment can then be pressed into receiving portions inside the connector elements of the multi-connector for a detachable connection. Subsequently, the multi-connector can be arranged at the tube roller pump together with the transfer system mounted thereon.

This second embodiment of the multi-connector according to aspects of the invention as adapter for transfer systems of any type furthermore has the advantage that the material of the multi-connector need not be bio-compatible as it is not in direct contact with the blood of the patient.

The means for locking the multi-connector in the therapy position can be formed, for instance, at the base member interconnecting the two connector elements. The means for locking the multi-connector in the therapy position may be provided in the area of the second connector element, however, or are constituted by the connector element itself. For example, the second connector element can equally be formed at least partly in cylindrical shape, wherein the cylinder axes thereof extend in parallel to each other. In this way it can be achieved that the first connector element can be used as pivot bearing about the cylinder axis of which the base member with the second connector element can be pivoted, wherein the second connector element can be pressed into an opposite receiving portion so as to achieve locking of the multi-connector in the therapy position.

The connecting base member between the two connector elements permits good manipulation of the multi-connector as especially a gripping surface can be formed at the same which can be used for moving the multi-connector during insertion and removal by a user. Also a single-handed manipulation is possible. In an embodiment of the invention at least one side face of the base member is S-shaped for this purpose. This shape can entail e.g. an ergonomic design of the multi-connector so that it can be gripped easily and safely. An S-shaped or even twisted shape having plural S-shaped surfaces in particular permits gripping and swiveling out also a multi-connector mounted at the pump housing, because in this way appropriate gripping areas can be formed which are accessible even in the mounted state. Consequently, no actuator is required to move the multi-connector out of the therapy position. Nor is it necessary to operate a switch or button to initiate the unthreading operation.

An S-shaped or differently shaped side face of the multi-connector can also be used as a geometrical encoding, however, by which the multi-connector can be specifically aligned at a pump housing when the pump housing is equally appropriately formed.

In an embodiment of the invention at the multi-connector furthermore means are provided by which the multi-connector can be held at the pump housing in a position in which it is arranged on the pump housing via the first connector element but is not locked with the pump housing aside the first connector element. Thus the afore-mentioned additional locking means are concerned by which the multi-connector can be held in an unthreading position, for instance after swiveling out at the pivot bearing, without the operator having to operate additional mechanisms so that the multi-connector does not swivel back again. These additional locking means can be materialized at the multi-connector by a bent spring element, for instance, that is arranged on the base member in the area of the first connector element. The curvature of the spring element extends substantially along the outer contour of the cylindrical area of the first connector element, with at least one stop element being disposed at the spring element. The stop element can be at least an indentation or bulging at the spring element. When the pump housing is appropriately shaped, by locking at the pump housing the multi-connector can be held at least in a swivel position.

Moreover, the invention comprises a pertinent medical device for extracorporeal blood treatment, comprising at least a tube roller pump including a pump housing having a bent bearing surface and a rotor rotating inside the bearing surface, wherein a tubing segment of an extracorporeal blood circulation can be introduced between the bearing surface and the rotor and blood can be supplied to the tubing segment via a feeding line, while blood can be discharged from the tubing segment via a discharging line. The multi-connector according to aspects of the invention is adapted to be mounted on the pump housing to which effect at the pump housing a receiving portion is provided into which the cylindrical area of the first connector element can be introduced, thereby a pivot bearing being formed by which the multi-connector is pivotable about the cylinder axis of the connector element. Furthermore, at the pump housing means for locking an area of the multi-connector at the pump housing are provided, said area being located aside the first connector element.

The means for locking the multi-connector at the pump housing can be formed, for example, by a receiving portion at the pump housing in which the second connector element can engage. As described in the foregoing already, for this purpose the second connector element may have a cylindrical shape so that it can be introduced into a groove-shaped receiving portion. The geometry and the dimensions of said groove-shaped receiving portion are chosen, for instance, so that the second connector element has to be forced over an edge of the receiving portion so as to engage in the groove of the receiving portion. This operation takes place during mounting of the multi-connector while during dismounting the second connector element has to be pulled over the stop edge out of the receiving portion so as to release the locking again. The multi-connector and/or the pump housing therefore should be formed elastically in any way so as to allow for the locking function.

In addition to these locking means aside the pivot bearing, further means are provided at the pump housing so as to be able to hold the multi-connector in at least a swivel position of the pivot bearing. For this, at the pump housing for example a stop catch is provided for locking with a spring element of the multi-connector.

It is further desirable to be able to fix the multi-connector in the therapy position also along the cylinder axis of the first connector element. For this, at the pump housing at least an elevation can be formed which contacts the base member of the multi-connector, when the multi-connector is mounted, and thus prevents displacement, because the multi-connector is positively connected to the pump housing in this direction.

Typically a pivoting cover by which at least the bearing surface and the rotor of the pump can be covered is arranged at the pump housing, wherein in an embodiment of the invention the cover is configured so that it forms a counter-bearing when the first connector element is introduced into the corresponding receiving portion. The geometries of the cover and of the multi-connector thus are matching.

The invention further comprises such medical device in which a multi-connector according to aspects of the invention is arranged at the pump housing.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
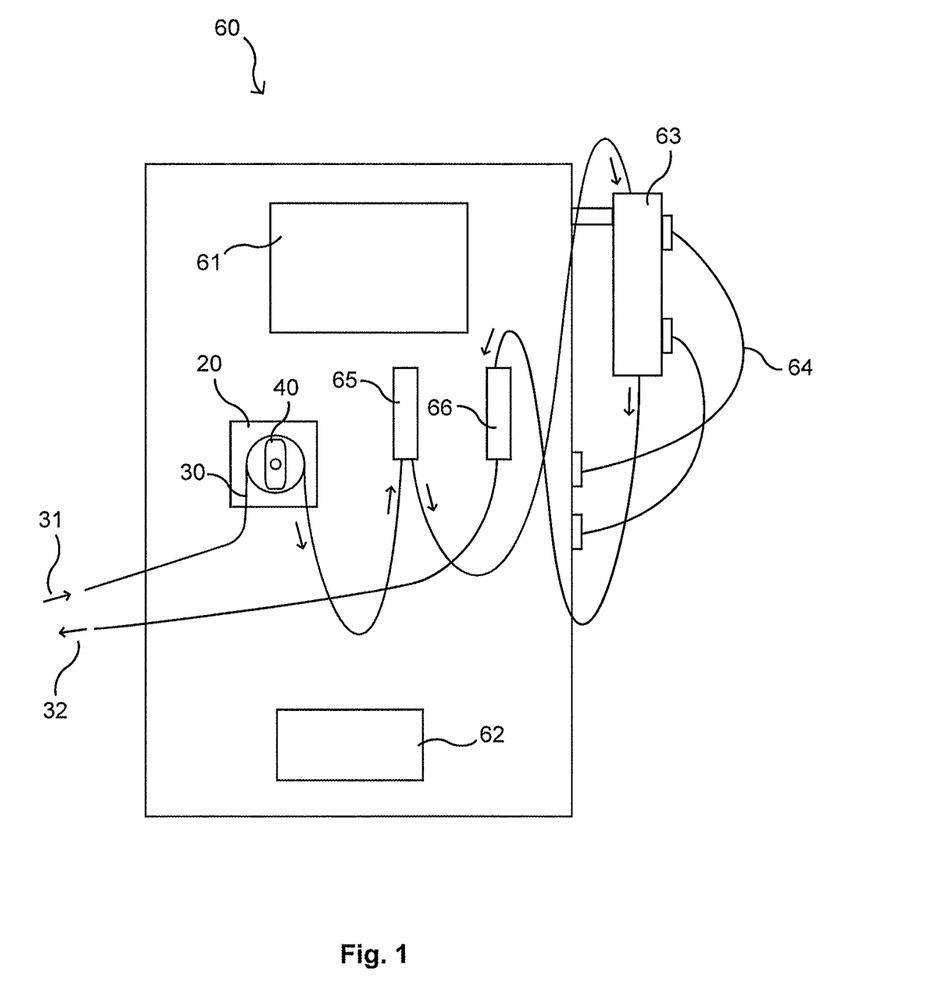
FIG. 1 a schematic representation of a medical device for extracorporeal blood treatment with a blood pump.

FIG. 1 shows a schematic representation of the essential basic components of a medical device or dialyser 60 for extracorporeal blood treatment including a blood pump, the latter being a tube roller pump. The tube roller pump includes a pump housing 20 which is typically arranged at the front side of the dialyser 60.

Arterial blood 31 of a patient is supplied to said tube roller pump and is fed through the extracorporeal blood circulation. After that the blood is returned to the patient as venous blood 32 again. The blood is fed by the pump through a transfer system connected to plural components of the dialyser, a tubing segment 30 of the transfer system being inserted in the blood pump and a rotor 40 feeding the blood through said tubing segment 30 in a peristaltic manner, as is evident from an enlarged view of FIG. 2.

After passing the blood pump the blood arrives at a dialyser 63 after having preferably passed an arterial air trap 65 before. In the dialyser 63 the blood is purified by substance exchange with a dialysate 64 fed to and discharged from the dialyser 63. After passing the dialyser 63 the blood arrives at a venous air trap 66 and is then supplied to the patient. This circulation of the patient's blood is marked by arrows in FIG. 1.

Parameters of the dialysis can be set and the therapy can be monitored via a display/input unit 61, which may be in the form of a touchscreen. The dialyser 60 further includes a control unit 62.

Figure 2:
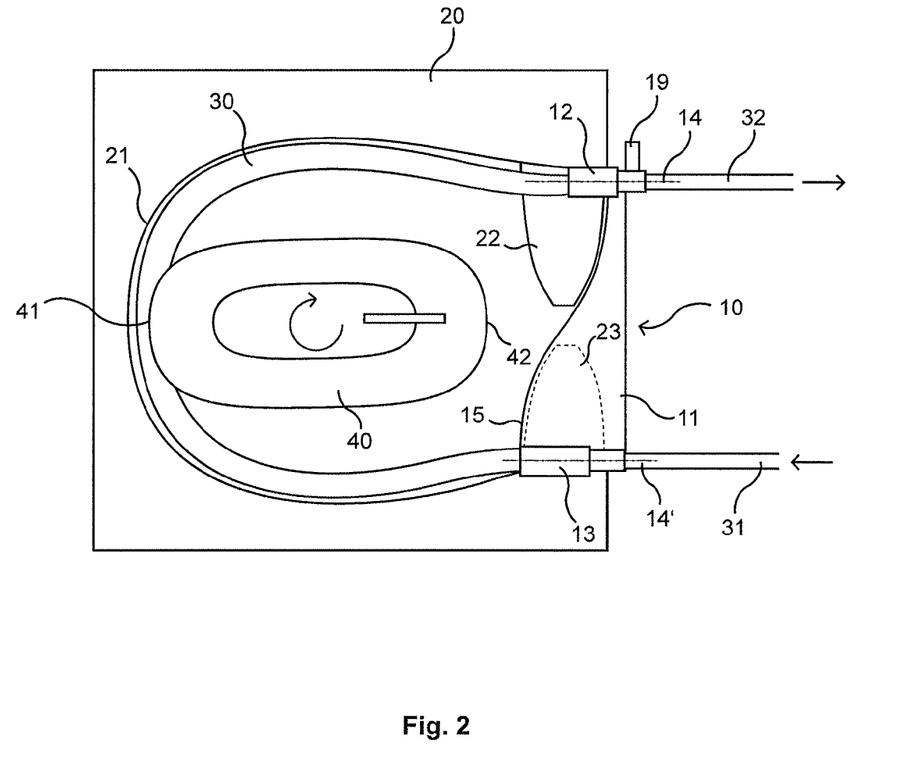
FIG. 2 a schematic representation of a tube roller pump including an inserted tubular piece and a multi-connector according to a first embodiment.

FIG. 2 illustrates a schematic representation of a tube roller pump including an inserted tubing segment 30 and a first embodiment of a multi-connector 10. The tube roller pump includes the pump housing 20 which is easily accessible for the operator of the device, the pump housing 20 being adapted to be covered by a cover 50 (not shown in FIG. 2) adapted to be pivoted e.g. upward via a hinge so as to get access to the tubing segment 30.

In the pump housing 20 a curved bearing surface 21 into which the tubing segment 30 can be inserted in loop shape is formed by an indentation in the housing so that its two tube ends protrude from the housing 20. The indentation can be formed to have a side face in the pump housing 20 which extends substantially evenly normal to the front side of the device or the bearing surface 21 is formed unevenly by a side face of the indentation which is concave or even twisted in itself.

Within the bearing surface 21 a rotor 40 having an elliptic circumference is arranged so that it can easily compress the tubing segment 30 during rotation at its vertices 41, 42 or rollers arranged thereon. By clockwise rotation of the rotor 40 the area of a compressed tubing segment 30 moves equally clockwise until the corresponding vertex 41 detaches from the tubing segment 30 again. At this time the opposite vertex 42 already contacts the tubing segment 30 again, however, so that blood is fed from the pump inlet to the pump outlet in a peristaltic manner in the respective area of the tubing segment 30 in which it is compressed by the rotor 40.

At the two ends of the tubing segment 30 the multi-connector 10 according to aspects of the invention is disposed to establish a connection to a feeding line 31 and a discharging line 32 through which blood is thus fed and discharged and via which the tubing segment 30 and the two lines 31 and 32 are detachably mountable to the pump housing 20, as will be described in detail further below. These lines 31, 32 are part of the extracorporeal blood circulation and are connected to various components such as air traps 65 and 66 and to the dialyser 63.

The multi-connector 10 comprises a base member 11 interconnecting two opposed connector elements 12 and 13 which can also be referred to as connectors. At least the connector element 12 has a cylindrical or hollow-cylindrical shape or has an outwardly and evenly curved external face. Hereby this connector element 12 can be introduced or inserted into an appropriately shaped, especially inwardly and evenly curved receiving portion 24 (cf. FIG. 3a) in the pump housing 20, no tool needed, wherefrom a pivot bearing or slide bearing is resulting about which the multi-connector 10 can be swiveled during mounting and dismounting. The second connector element 13 preferably equally has a cylindrical or hollow-cylindrical shape, wherein also a cylinder having stepped external faces or stop faces can be provided. The cylinder axes 14 and 14' of the two connector elements 12, 13 extend in parallel to each other and transversely to the longitudinal extension of the base member 11 or the multi-connector 10 so that the two lines 31, 32 are guided into the pump and out of the pump equally in parallel.

The multi-connector 10 thus can be swiveled out of the plane of projection about the pivot point at the connector element 12. In the swiveled-in position means are provided by which the multi-connector 10 is lockable at the pump housing

20. For example, the second connector element 13 is shaped in such way that it engages in a receiving portion 25 in the pump housing 20 when it is forced against the pump housing 20. However, it can also be released from said receiving portion 25 by slightly pulling when the multi-connector 10 is swiveled out of the plane of projection of FIG. 2. The base member 11 of the multi-connector 10 may therefore be slightly elastic in itself so as to permit engaging or positive locking in the receiving portion 25. However, it can also be relatively rigid, wherein in this case the receiving portion 25 would be configured to be elastic in the pump housing 20.

In the view shown in FIG. 2 at least a left side face 15 of the base member 11 is S-shaped. This side face 15 constitutes a geometrical encoding, wherein the encoding can also take other suitable shapes. Hereby it is possible to align the multi-connector 10 specifically at the pump housing 20, wherein it is further supported against a movement along the cylindrical axes 14, 14' at the pump housing 20. For this, at the pump housing 20 e.g. an appropriately shaped supporting element 22 is provided in the form of an elevation at the pump housing 20. The side face 15 of the base member 11 is adjacent to said supporting element 22. Thus the multi-connector 10 can be aligned at the supporting element 22 and at the same time cannot be pressed into the pump in the area of the pump outlet.

The base member 11 may be in the form of an inexpensive disposable and consists of a structure of three-dimensional faces and/or braces forming outwardly open hollows so that on its other side the side face 15 can simultaneously be adjacent to a supporting element 23 shown in broken lines below the multi-connector 10. This supporting element 23 is equally in the form of an elevation at the pump housing 20. Thus the multi-connector 10 cannot be laterally pulled out of the pump at the pump inlet.

Further faces of the base member 11 can be equally bent or even twisted in themselves, whereby a gripping surface can be formed on the right side of the base member 11, for example. An operator can grip the multi-connector 10 at said gripping surface to firstly insert it into the upper receiving portion 24 and then swivel it into the plane of projection and lock it in the lower receiving portion 25. To explain this operation in detail the FIGS. 3a and 3b illustrate a first side view of the multi-connector 10, with this view in FIG. 2 corresponding to a view from the right side.

Figure 3A:
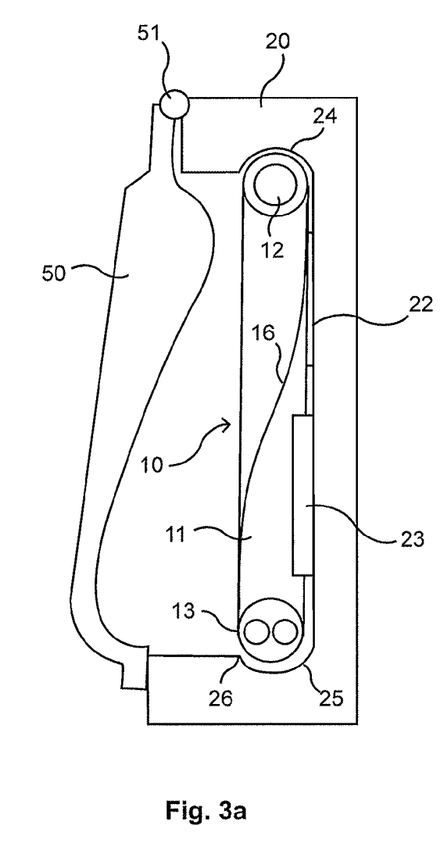
FIG. 3a a first schematic side view of a tube roller pump according to FIG. 2.
Figure 3B:
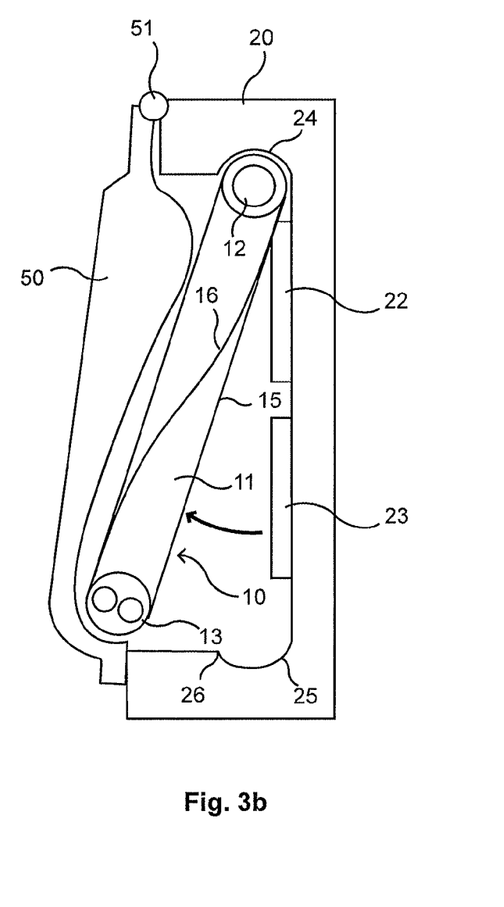
FIG. 3b a schematic side view according to FIG. 3a where the multi-connector is swiveled out.

FIG. 3a illustrates an inserted multi-connector 10 the upper connector element 12 of which is introduced into a semicircular receiving portion 24 in the pump housing 20. The cylindrical shape of the connector element 12 and the receiving portion 24 in this position results in a slide bearing having a pivot point or a pivot axis about which the multi-connector 10 can be pivoted. The lower connector element 13 is engaged in a receiving portion 25. This can be achieved, for instance, by a semicircular receiving portion 25 having an edge 26 acting as stop edge (left edge of the receiving portion 25 in FIGS. 3a and 3b) projecting into the swivel area of the multi-connector 10 about the pivot axis over which the connector element 13 has to be forced before it enters the receiving portion 25. However, the locking can be performed at other component parts as well. For example, the multi-connector 10 can also be locked at the inside of the supporting element 23 by an appropriate geometry. This is the therapy position of the multi-connector 10 (threading position).

In this view it is also visible that the lower connector element 13 has two orifices for connecting lines which on the other side open into a joint tube adapted to be connected to the tubing segment 30 in the pump. In this way different lines can be connected. For example, one orifice can be used for the blood supply and another port can be used for pressure measurement. Furthermore at the upper connector element 12 another connecting tube 19 can be provided which is merely shown in FIG. 2, however, and extends normal to the cylinder axis 14. A further line which may be a heparin supply, for example, can equally be connected to said additional port 19.

Moreover the supporting element 23 which prevents the multi-connector 10 from being pulled out of the pump is evident, wherein the other supporting element 22 is indicated behind the multi-connector 10. The pump housing 20 is further covered by a hinged cover 50 pivotable about an upper hinge 51. The multi-connector 10 can be pulled against said cover 50 over a gripping surface formed at the base member 11 during dismounting, as is shown in FIG. 3b. This position is a defined second position which can also be referred to as unthreading position.

For this, the multi-connector 10 can be gripped at its base member 11 and swiveled about the pivot point in the upper receiving portion 24 as shown by the arrow. For this purpose, a further S-shaped area 16 of the base member 11 can be shaped so that the operator can safely grip the multi-connector 10 in this area. Then the locking of the lower receiving portion 25 has to be overcome by pulling the lower connector element 13 over the stop edge 26. The closed cover 50 of the pump serves as counter-bearing and at the same time as abutment for the multi-connector 10 in the second end position.

Figure 4A:
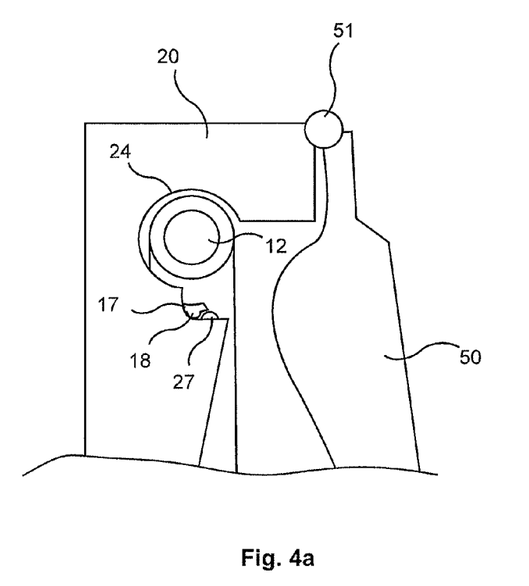
FIG. 4a a second schematic side view of a tube roller pump according to FIG. 2.
Figure 4B:
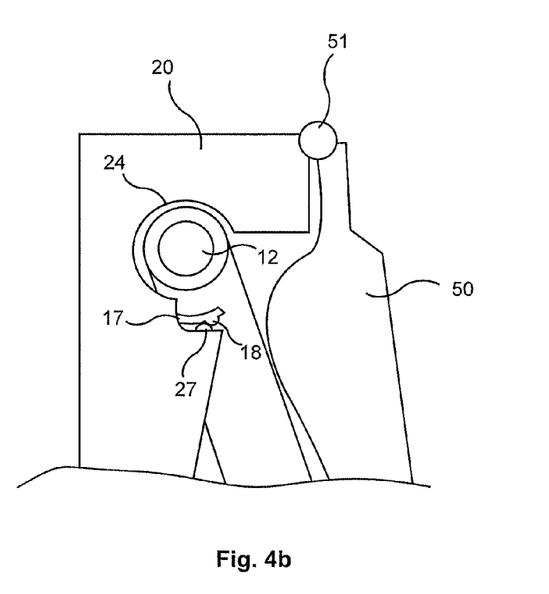
FIG. 4b a schematic side view according to FIG. 4a where the multi-connector is swiveled out.

In order to be able to hold the multi-connector 10 in the unthreading position a spring mechanism is provided at the upper pivot point, for instance. The functioning of said spring mechanism can be inferred from FIGS. 4a and 4b showing a view onto the multi-connector of FIG. 2 from the left, with merely an enlarged cut-out of the upper pivot point being represented, however. In FIG. 4a the multi-connector 10 is shown in the therapy position again, wherein on this side of the base member 11 an arc-shaped spring element 17 is arranged at the base member 11. Said spring element 17 extends substantially along the outer contour of the connector element 12 and includes a stop element in the form of an elevation 18. Said elevation 18 in this position of the multi-connector 10 abuts against a stop catch 27 formed at the pump housing 20. The multi-connector 10 is thus locked with the pump housing 20 at the upper and lower connector elements 12, 13.

When swiveling the multi-connector 10 out of the therapy position into the unthreading position, it has to be rotated not only out of the lower locking but also out of the upper locking. This is shown in FIG. 4b, wherein it is visible that upon pivoting about the pivot point the upper connector element 12 was pulled with the stop element 18 over the stop catch 27 at the pump housing 20. The multi-connector 10 can be held in this position, as the stop element 18 is now adjacent to the stop catch 27 from the other side and will not slip back or swivel back solely by the weight of the multi-connector 10. The pump cover 50 may serve as counter-bearing.

Figure 5:
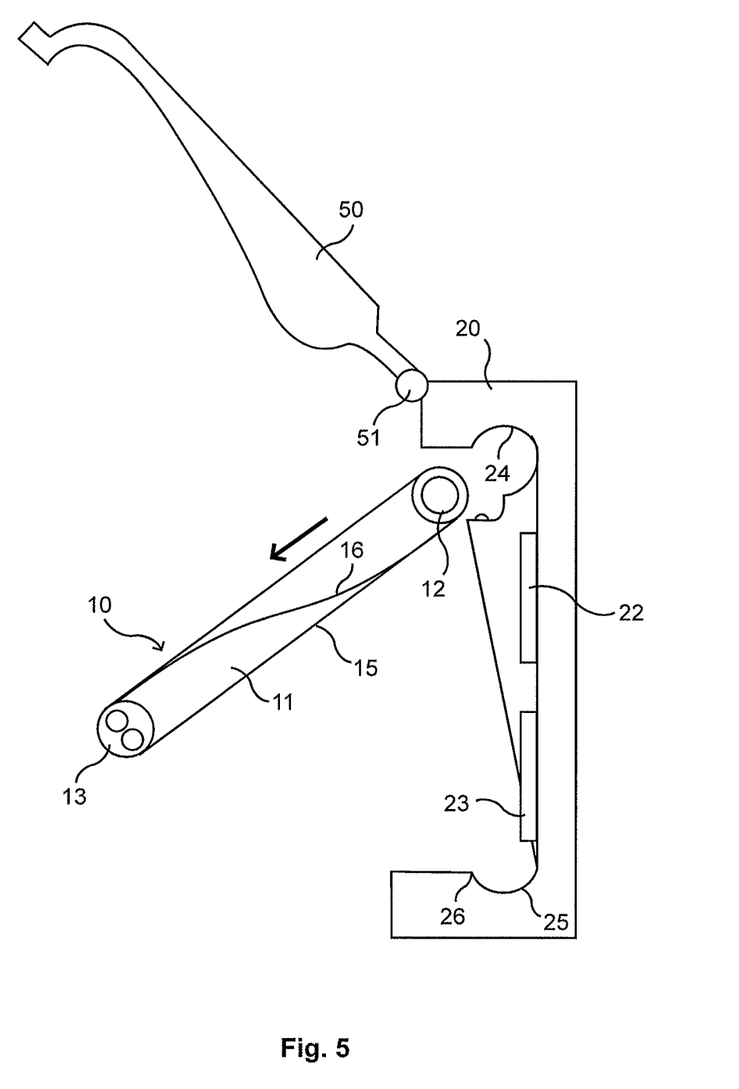
FIG. 5 a schematic side view according to FIG. 3a upon removing the multi-connector.

FIG. 5 illustrates the removal of a multi-connector 10 from the pump housing 20, the pump cover 50 having been swiveled upward about the hinge 51 before so as to remove the multi-connector 10. However, also other types of covers and opening mechanisms can be provided. After the swivel motion according to FIGS. 3b and 4b, respectively, the multi-connector 10 can now be removed from the upper receiving portion 24, which is illustrated by an arrow.

The locking operations are preferably facilitated by the fact that the base member 11 is formed to be elastic by its geometry of plural bent surfaces. Therefore the material used for the base member 11 and/or the connectors 12, 13 may be a hard plastic allowing for such elasticity.

In order to assist the correct mounting of the multi-connector 10 on the pump housing 20, color encodings can be provided. Depending on the embodiment, incorrect mounting can also be prevented by the specific shape of the component and of the pump housing 20.

Figure 6:
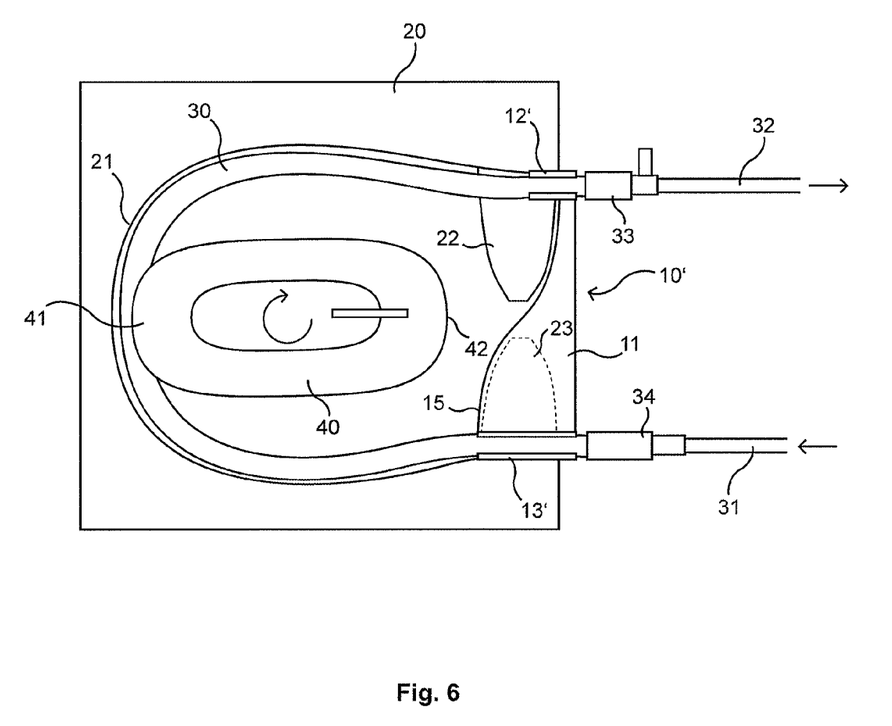
FIG. 6 a schematic representation of a tube roller pump including an inserted tubular piece and a multi-connector in the form of an adapter according to a second embodiment.

FIG. 6 illustrates a schematic representation of a tube roller pump including an inserted tubing piece and a multi-connector 10' according to a second embodiment in which the multi-connector 10' is used as an adapter for a transfer system. The structure of said multi-connector 10' substantially corresponds to the structure according to the first embodiment in which the tubing segment 30 and the feeding and discharging lines 31, 32 are connected directly and tightly to the multi-connector 10. The transfer system to be connected again consists at least of a tubing segment 30 and the feeding and discharging lines 31 and 32; however, the latter are connected to the tubing segment 30 via simple connecting elements 33 and 34.

Figure 7:
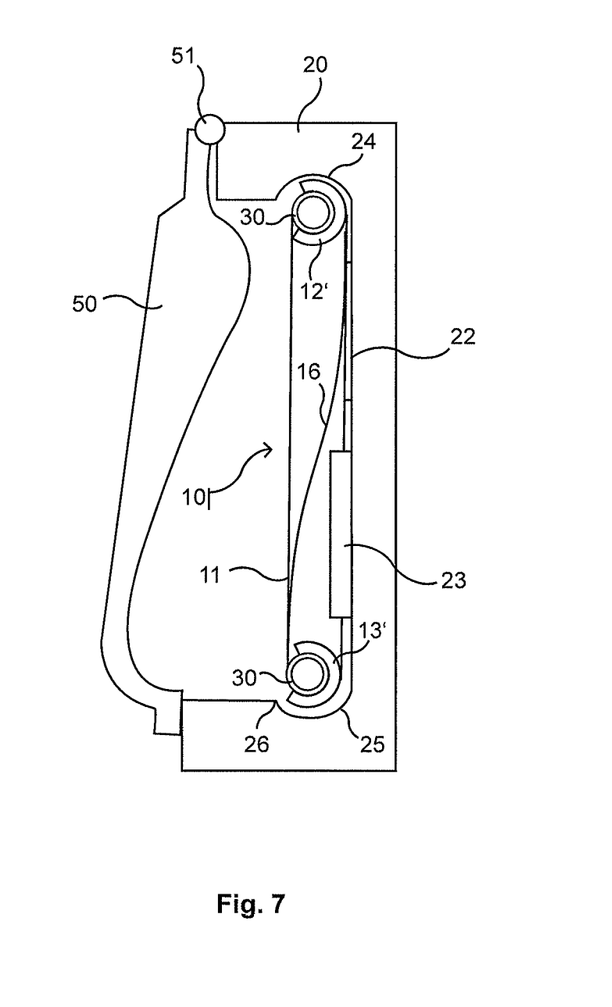
FIG. 7 a schematic side view of a tube roller pump according to FIG. 6.

In order to be able to benefit from the advantages of the multi-connector 10' according to aspects of the invention for such standard transfer system the connector elements 12' and 13' of the multi-connector adapter 10' are shaped such that the tube of the tubing segment 30 can be detachably arranged on the same. For this, the connector elements 12' and 13' are configured as receiving portions, which can be obtained by hollow-cylindrical connector elements 12', 13', for example, having a longitudinal section into which the tubing segment 30 can be pressed. This insertion of the tubing segment 30 into the connector elements 12' and 13' can also be inferred from the side view of FIG. 7.

After the therapy the tubing segment 30 can be removed from the adapter 10' again and a new tubing segment can be attached thereto so that the adapter constitutes a re-usable component.

In an alternative embodiment of the multi-connector as an adapter the connector elements are formed so that the connecting elements 33 and 34 of the transfer system to be arranged can be disposed at the connector elements of the multi-connector so as to connect the transfer system to the adapter. In this case, too, locking connections are useful. Also a connection via the feeding and discharging lines or a combination of plural types of connection would be possible.

The invention claimed is:

1. A multi-connector for arranging a tubing segment and feeding and discharging lines of an extracorporeal blood circulation on a tube roller pump, the multi-connector comprising at least a base member and two connector elements for connecting the respective ends of the tubing segment to the feeding line and the discharging line, wherein
the connector elements are arranged on two opposed sides of the base member,
wherein an outer contour of a first connector element includes at least one slide bearing portion which is inserted into a recess correspondingly formed to the slide bearing portion in a pump housing of the tube roller pump, and
wherein a pivot bearing is formed by the slide bearing portion of the first connector element such that the multi-connector is pivotable about a cylinder axis of the first connector element when the first connector element is inserted into the recess in the pump housing;
the multi-connector includes means spaced apart from the first connector element for locking the multi-connector with the pump housing of the tube roller pump; and
at the multi-connector means are provided by which the multi-connector can be held at the pump housing in a position in which it is guided at the pump housing by the first connector element but is not detachably fastened to the pump housing via the means for locking.

2. The multi-connector according to claim 1, wherein the connector elements are tightly connected to the tubing segment and the feeding and discharging lines.

3. The multi-connector according to claim 1, wherein each of the connector elements includes means for detachably connecting the tubing segment and the feeding and discharging lines to the multi-connector.

4. The multi-connector according to claim 1, wherein the means for locking are provided in the area of the second connector element or are formed by the connector element itself.

5. The multi-connector according to claim 1, wherein both connector elements have a hollow-cylindrical shape, with the cylinder axes thereof extending in parallel to each other.

6. The multi-connector according to claim 1, wherein a gripping surface is formed at the base member between the two connector elements.

7. The multi-connector according to claim 1, wherein the base member has at least a geometrical encoding.

8. A multi-connector for arranging a tubing segment and feeding and discharging lines of an extracorporeal blood circulation on a tube roller pump, the multi-connector comprising at least a base member and two connector elements for connecting the respective ends of the tubing segment to the feeding line and the discharging line, wherein
the connector elements are arranged on two opposed sides of the base member, a first connector element including at least one portion having an outwardly and evenly curved outer contour that permits a defined pivoting motion of the multi-connector about a pivot axis when it interacts with an appropriately inwardly and evenly curved recess in the pump housing of the tube roller pump;
the multi-connector includes means spaced apart from the first connector element for locking the multi-connector with the pump housing of the tube roller pump;
at the multi-connector means are provided by which the multi-connector can be held at the pump housing in a position in which it is guided at the pump housing by the first connector element but is not detachably fastened to the pump housing via the means for locking; and
in the vicinity of the first connector element a bent spring element the bending of which substantially follows the curved outer contour section of the first connector element is arranged on the base member, wherein at least one stop element is disposed at the spring element.

9. The multi-connector according to claim 8, wherein the stop element is at least an indentation or a bulging at the spring element.

10. A medical device for extracorporeal blood treatment comprising at least a tube roller pump including a pump housing having a bent bearing surface and a rotor rotating inside the bearing surface, wherein a tubing segment of an extracorporeal blood circulation can be introduced between the bearing surface and the rotor and blood can be fed to the tubing segment via a feeding line, while blood can be discharged from the tubing segment via a discharging line, wherein
a multi-connector according to claim 1 can be arranged on the pump housing, for which purpose on the pump housing a first inwardly and evenly curved receiving portion is provided into which the first connector element can be introduced, thereby a pivot bearing being formed by which the multi-connector is pivotable about the pivot axis, and at the pump housing means for locking are equally provided which are adapted to interact with the means for locking provided at the multi-connector so that the multi-connector can be detachably fastened to the pump housing at least in a relative position.

11. The medical device according to claim 10, wherein the means for locking the multi-connector at the pump housing are formed by a second inwardly and evenly curved receiving portion at the pump housing in which the second connector element is adapted to be engaged.

12. The medical device according to claim 10, wherein means for fixing the multi-connector along the pivot axis of the first connector element are provided at the pump housing.

13. The medical device according to claim 12, wherein at the pump housing at least one elevation is formed which is adjacent to the base member of the multi-connector when the multi-connector is mounted.

14. The medical device according to claim 10, wherein a stop catch for locking with a bent spring element of the multi-connector in the vicinity of the first connector element is provided at the pump housing, whereby the multi-connector can be held in at least a pivoting position of the pivot bearing.

15. The medical device according to claim 10, wherein a pump cover for covering the bearing surface and the rotor is arranged at the pump housing, the cover being shaped so that it forms a counter-bearing when the first connector element is introduced into the receiving portion.

* * * * *